(12) United States Patent
Purchio et al.

(10) Patent No.: US 8,467,493 B2
(45) Date of Patent: Jun. 18, 2013

(54) METHODS AND COMPOSITIONS FOR IMAGING ATHEROSCLEROTIC PLAQUES

(75) Inventors: Anthony F. Purchio, Taylorsville, UT (US); Ali Bahadur, South Jordan, UT (US); Sergio Vasquez, South Jordan, UT (US)

(73) Assignee: Numira Biosciences, Inc., Salt Lake City, UT (US)

( * ) Notice: Subject to any disclaimer, the term of this patent is extended or adjusted under 35 U.S.C. 154(b) by 162 days.

(21) Appl. No.: 12/684,793

(22) Filed: Jan. 8, 2010

(65) Prior Publication Data

US 2010/0172463 A1 Jul. 8, 2010

Related U.S. Application Data

(60) Provisional application No. 61/143,380, filed on Jan. 8, 2009.

(51) Int. Cl.
*G01N 23/00* (2006.01)
*G06K 9/00* (2006.01)

(52) U.S. Cl.
USPC .............................................. 378/4; 382/131

(58) Field of Classification Search
None
See application file for complete search history.

(56) References Cited

U.S. PATENT DOCUMENTS

| | | |
|---|---|---|
| 2003/0140357 A1 | 7/2003 | Herrera et al. |
| 2004/0131546 A1 | 7/2004 | Misselwitz et al. |
| 2005/0036904 A1 | 2/2005 | Kajander et al. |
| 2007/0190054 A1 | 8/2007 | Ashkenazi et al. |
| 2007/0213641 A1 | 9/2007 | Francis |
| 2008/0031816 A1 | 2/2008 | Keller |
| 2008/0240527 A1 | 10/2008 | Keller |
| 2008/0260646 A1 | 10/2008 | Keller et al. |
| 2008/0260714 A1 | 10/2008 | Barry et al. |
| 2009/0080600 A1 | 3/2009 | Keller et al. |
| 2009/0210950 A1 | 8/2009 | Purchio |
| 2010/0183212 A1 | 7/2010 | Purchio et al. |

FOREIGN PATENT DOCUMENTS

WO  WO 2007/089641  8/2007

OTHER PUBLICATIONS

Choudhury et al. Atherosclerotic Lesions in Genetically Modified Mice Quantified in Vivo by Non-Invasive High-Resolution Magnetic Resonance Microscopy; Atherosclerosis, vol. 162 (2002) pp. 315-321.*
Goel et al. Site-Specific Effects of PECAM-1 on Atherosclerosis in LDL Receptor-Deficient Mice; Arteriosclerosis, Thrombosis, and Vascular Biology, vol. 28 (2008). 1996-2002.*
Assmann, G. et al., "Quantification of High-Density-Lipoprotein Cholesterol by Precipitation with Phosphotungstic Acid/$MgCl_2$,", *Clinical Chemistry*, vol. 29, No. 12 (1983).
Brown, L. G., "A Survey of Image Registration Techniques", *ACM Computing Surveys*, vol. 34, No. 4, 325-376, (1992).
Jacobs, R.E. et al., "Towards a microMRI atlas of mouse development", *Comput Med Imaging Graph* 23, 15-24 (1999).
Bentley, M.D., et al., "*The Use of Microcomputed Tomography to Study Microvasculature in Small Rodents,*" American J. of Physiology, Regulatory, Integrative and Comp. Physiol., v. 282, R1267-R1279, (2002).
Cavanaugh, D., et al., "*In Vivo Respiratory-Gated Micro-CT Imaging in Small Animal Oncology Models,*" Molecular Imaging, v. 3, n. 1, p. 55-62 (2004).
Ritman, E.L., *Molecular Imaging in Small Animals-Roles for Micro-CT*, J. Of Cellular Biochemistry, Supplement 39, p. 116-124 (2002).
Watz, H., et al., *Micro-CT of the Human Lung: Imaging of Alveoli and Virtual Endoscopy of an Alveolar Duct in a Normal Lung and in a Lung with Centrilobular Emphysema-Initial Observations*, Radiology, v. 236, p. 1053-1058 (2005).

\* cited by examiner

*Primary Examiner* — Allison Ford
*Assistant Examiner* — Paul Martin
(74) *Attorney, Agent, or Firm* — Morgan, Lewis & Bockius LLP

(57) ABSTRACT

The present invention relates in general to compositions, processes and apparatus for imaging, and in particular for preparation, collection and processing of images of atherosclerotic plaques, including images obtained from X-ray microscopic computed tomography.

4 Claims, 1 Drawing Sheet

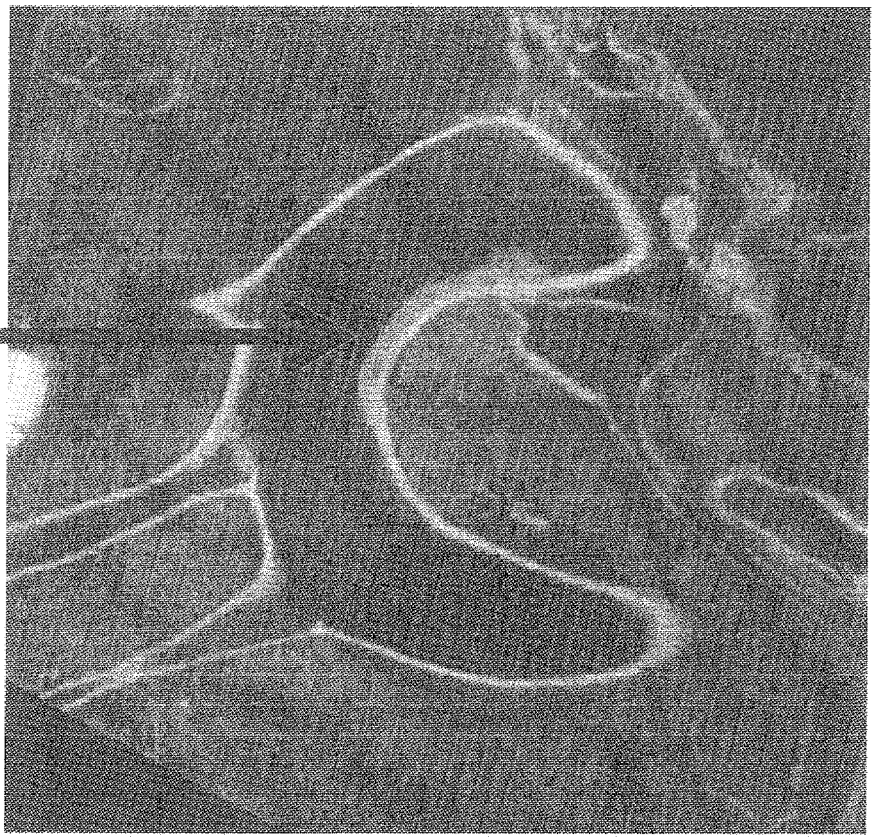
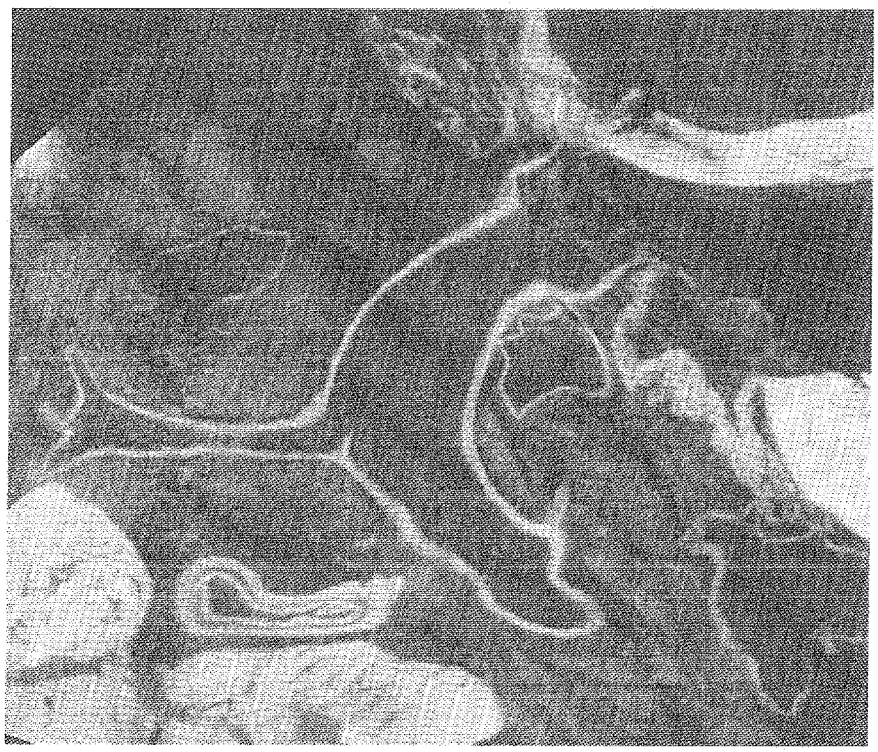

METHODS AND COMPOSITIONS FOR
IMAGING ATHEROSCLEROTIC PLAQUES

CROSS-REFERENCE TO RELATED APPLICATIONS

This application claims benefit of priority to U.S. Provisional Patent Application Ser. No. 61/143,380, filed Jan. 8, 2009, which is hereby incorporated by reference in its entirety.

FIELD OF THE INVENTION

The present invention relates in general to compositions, processes and apparatus for imaging, and in particular for preparation, collection and processing of images of atherosclerotic plaques, including images obtained from X-ray microscopic computed tomography.

BACKGROUND OF THE INVENTION

A key alleviation and cure of atherosclerosis is early detection and diagnosis so that the proper treatment can be initiated. Accurately identifying the presence, location, and size of an atherosclerotic plaque is thus diagnostically significant to establish a proper course of treatment, the need for surgical intervention, and the site of surgery or therapy. The ability to provide detailed images of such plaques is a key to providing such information.

MicroCT-based virtual histology imaging provides a high resolution system that can be simple to implement, relatively inexpensive, and more rapid than comparable methods of phenotyping anatomy, particularly anatomy of tissue samples, whole organs as well as whole organisms. One way to improve the level of detail that can be obtained from microCT virtual histology is through improvements in the way specimens are prepared and stained prior to being scanned.

SUMMARY OF THE INVENTION

Accordingly, the present invention provides methods and compositions for preparing specimens for image acquisition in microCT virtual histology as well as other imaging systems.

In one aspect, the present invention provides a method for detecting an atherosclerotic plaque. This method includes the step of incubating a specimen in a staining composition to produce a stained specimen. The stained specimen comprises an aorta, and the staining composition includes a 5% PTA solution. This method further includes the step of scanning the stained specimen in an X-ray tomography scanner to produce a microCT image of said stained specimen. The microCT image of the stained specimen provides the ability to detect the presence of an atherosclerotic plaque in the aortic specimen.

BRIEF DESCRIPTION OF THE FIGURES

FIG. 1 shows a microCT image of a mouse aorta with no atherosclerotic plaques present (left panel) and of a mouse aorta with atherosclerotic plaques present (right panel, arrow).

DETAILED DESCRIPTION OF THE PREFERRED EMBODIMENTS

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. It will be apparent to one of skill in the art that these additional features are also encompassed by the present invention.

Definitions

As used herein and in the appended claims, the singular forms "a," "an," and "the" include plural referents unless the context clearly dictates otherwise. Thus, for example, reference to "an agent" refers to one agent or mixtures of such agents, and reference to "the method" includes reference to equivalent steps and methods known to those skilled in the art, and so forth.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

As used herein, a "specimen" is a biological specimen, which encompasses cells, tissues, organs and whole organisms. The term "specimen" is used interchangeably herein with the term "sample".

As used herein, the term "organism" refers to any living entity comprised of at least one cell. A living organism can be as simple as, for example, a single eukaryotic cell or as complex as a mammal. The term "organism" encompasses naturally occurring as well as synthetic entities produced through a bioengineering method such as genetic engineering.

As used herein, the term "tissue" includes cells, tissues, organs, blood and plasma.

The term "identifying" (as in "identifying an anatomical feature") refers to methods of analyzing an object or property, and is meant to include detecting, measuring, analyzing and screening for that object or property.

A "property" is any biological feature that can be detected and measured.

The term "diagnosing disease" encompasses detecting the presence of disease, determining the risk of contracting the disease, monitoring the progress and determining the stage of the disease.

The "determining effectiveness of a treatment" includes both qualitative and quantitative analysis of effects of a treatment. Determining effectiveness of a treatment can be accomplished using in vitro and/or in vivo method. Determining effectiveness of a treatment can also be accomplished in a patient receiving the treatment or in a model system of the disease to which the treatment has been applied. In general, determining effectiveness of a treatment includes measuring a biological property at serial time points before, during and after treatment to evaluate the effects of the treatment.

"Treatment" generally refers to a therapeutic application intended to alleviate, mitigate or cure a disease or illness. Treatment may also be a therapeutic intervention meant to improve health or physiology, or to have some other effect on health, physiology and/or biological state. Treatment includes pharmacological intervention, radiation therapy, chemotherapy, transplantation of tissue (including cells, organs, and blood), and any other application intended to affect biological or pathological conditions.

The term "subject" refers to an organism that is the recipient of a biological and/or therapeutic intervention. A subject can be any organism, including cells, animals, and plants.

The term "patient" refers to a human subject that has a disease or has the potential of contracting a disease.

The term "microCT" refers to X-ray microscopic computed tomography.

The term "virtual histology" refers to methods by which specific tissues can be visualized using stains of the invention.

Overview

The present invention provides compositions and methods for imaging specimens. In particular, the present invention provides compositions and methods for using microCT virtual histology methods to obtain images of atherosclerotic plaques.

In one aspect, the present invention provides stains for preparing specimens for imaging. Stains of the invention are in specific embodiments tailored to improve the resolution of images obtained from regions of the cardiovascular system, such as the aorta and/or the heart.

In a further aspect, the present invention provides methods for obtaining images of specimens prepared using stains of the invention. In specific embodiments, imaging is accomplished using microCT virtual histology methods.

The methods and compositions of the present invention can be used in accordance with and/or in combination with the teachings of U.S. application Ser. No. 12/162,376, filed Oct. 15, 2008; Ser. No. 11/575,057, filed Jan. 29, 2008; Ser. No. 11/888,995, filed Aug. 3, 2007; Ser. No. 11/839,414, filed Aug. 15, 2007; Ser. No. 12/389,094, filed Feb. 19, 2009; 61/143,380, filed Jan. 8, 2009; and 61/230,574, filed Jul. 31, 2009, each of which is hereby incorporated by reference in its entirety for all purposes, including all drawings, examples, and disclosure.

Preparing Specimens for Imaging

In one aspect, the present invention provides methods and compositions for preparing specimens for acquisition of images. Preparing specimens for imaging includes dissection and further incisions upon the dissected specimen, fixing the specimens in one or more fixatives, staining the specimens in one or more staining agents that may include one or more additives, and further introducing additional compositions to improve the contrast between specific anatomical features.

In further embodiments, combinations of preparation methods are used to process specimens for imaging. As will be appreciated, any combination of such preparation methods described herein and known in the art can be used in accordance with the present invention. In some embodiments, staining agents are optionally combined with a buffer and/or a fixative and/or a cross-linking agent and/or a reporter substrate for a reporter gene product. As will be appreciated, any combination of such materials can be used to stain specimens in accordance with the present invention.

In a further aspect, microCT methods of the present invention provide high resolution, non-destructive analysis of the status, integrity and development of biological tissues. In some embodiments, these biological tissues represent a disease condition, such as atherosclerosis. The sensitivity and specificity of microCT-based analyses provides a rapid and inexpensive method that enhances visualization and analysis of complex global 3-dimensional organization. Unlike traditional histology, which requires meticulous slicing and individual examination, the methods of the present invention includes staining specimens with specific dyes and scanning them with microscopic computed tomography (microCT), which provides a high resolution image of the whole specimen without the need for the slices required in other imaging modalities. The methods of the present invention provide a digital visualization with the capability of providing a number of measurements of various anatomical features of the specimen. Such measurements include without limitation distance, area and volume of such anatomical features.

Staining Compositions

In one aspect, the invention provides staining compositions for preparing specimens for acquisition of images, such as microCT images. Some staining compositions and their components are known in the art and described, for example, in International Publication No. WO/2007/089641, filed on Jan. 26, 2007 and U.S. application Ser. No. 11/575,057, filed Oct. 23, 2008, each of which is hereby incorporated by reference in its entirety for all purposes and in particular for all teachings related to preparing specimens for imaging, particularly microCT imaging. In general, such stains include an electron dense staining agent which produces an electron dense staining of one or more components of the specimen. Electron dense staining agents generally include a metal atom or ion.

In one aspect, staining compositions of the invention include staining agents. Exemplary staining agents of use in the present invention include metals such as osmium (e.g., osmium tetroxide), tungsten (e.g., phosphotungstic acid, sodium tungstate), molybdenum (e.g., ammonium molybdate, phosphomolybdic acid), the noble metals, e.g., (platinum (e.g., cisplatin), gold (e.g., sodium chloroaurate)), bismuth (e.g., bismuth subnitrate), cadmium (e.g., cadmium iodide), iron (e.g., ferric chloride, potassium ferricyanide, potassium ferrocyanide), indium (e.g., indium trichloride), lanthanum (e.g., lanthanum trichloride), lead (e.g., lead acetate, lead citrate, lead nitrate), ruthenium (e.g., ruthenium red), silver (silver nitrate, silver proteinate, silver tetraphenylporphyrhin), thalium (e.g., thallium nitrate), uranium (e.g., uranyl acetate, uranyl nitrate) and vanadium (vanadyl sulfate). Other appropriate metals of use in the methods of the invention will be apparent to those of skill in the art.

In further embodiments, organic stains are also of use in the staining compositions of the present invention. An exemplary organic stain is ethidium bromide.

The staining agent is present in the staining composition in any concentration useful to provide a desired level of contrast in the image of the specimen. Appropriate concentrations of a selected staining agent are readily determinable by those of skill in the art without resort to undue experimentation. For example, arrays of staining compositions including a single staining agent are prepared. Each composition is used to stain a specimen. The level of staining of each specimen by each staining composition is determined by acquiring a microCT image of each of the stained specimens.

In an exemplary embodiment, the staining agent is present in the staining composition in an amount from about 0.01 weight percent to about 10 weight percent, preferably from about 0.1 weight percent to about 5 weight percent, more preferably from about 1 weight percent to about 3 weight percent.

In further embodiments, the specimen is stained in a combination of staining agents. Such a combination of staining agents may include two or more of any staining agents described herein and known in the art.

Optionally, staining compositions of the invention further include at least one buffer component. The buffer is present in any concentration that is useful to provide a desired level of staining of the specimen, as evidenced, in one embodiment, by obtaining a desired level of contrast in a microCT image of the stained tissue. A buffer that has a different osmotic concentration than the tissue is optionally used in the process of stain penetration so as to accelerate transfer of stain molecules into components of the tissue, e.g., tissue cells.

Exemplary buffer concentrations for staining compositions of the invention range from about 0.01 M to about 1.0 M. In further exemplary embodiments, the buffer concentrations are in the range of about 0.05 to about 0.90, about 0.10 to about 0.80, about 0.20 to about 0.70, about 0.30 to about 0.60 and about 0.40 to about 0.50 M. In some embodiments, the buffer is a cacodylate buffer, e.g., sodium cacodylate trihydrate. In some embodiments, the buffer is a phosphate buffer. Other buffers known in the art may also be used in accordance with the present invention.

In further embodiments, staining compositions include at least one fixative or cross-linking agent component such as glutaraldehyde, formaldehyde, alcohols, or a combination of these. In exemplary staining compositions, the fixative or cross-linking agent is present in a concentration range of from about 0.05% to about 5%, preferably from about 0.1% to about 3% and more preferably from about 1% to about 1.5%.

In still further embodiments, staining compositions of the invention may also include a tissue penetration enhancing agent component. A representative tissue penetration enhancing agent is DMSO.

In further embodiments, staining compositions of the invention include both the staining agent and a species that is indicative or confirmative of the presence of a reporter gene through direct interaction with that gene or with a product of the reporter gene. In one embodiment, the reporter gene product forms a complex with the species recited above and the staining agent. The resulting agent is detectable by an imaging modality, e.g., an X-ray imaging modality, such as microCT.

In yet further embodiments, staining compositions of the invention may include at least one additive component. Such additives can be useful for semi-automated computational analysis of the resultant images, because these additives can help preserve bone landmarks (for example, trabecular structures). Preservation of bone landmarks allows data sets to be iteratively overlaid with accuracy. In specific embodiments, these additives include aqueous calcium. In further embodiments, aqueous calcium in the concentration of about 0.1 to about 5 M is used. In still further embodiments, aqueous calcium in the concentration of about 0.2 to about 4, about 0.3 to about 3, about 0.4 to about 2, and about 0.5 to about 1 M is used in staining compositions of the invention. In further specific embodiments, additives used in staining compositions of the invention include without limitation: calcium, potassium, manganese, magnesium, silica, iron, zinc, selenium, boron, phosphorus, sulfur, chromium, hydroxyapatite. As will be appreciated, such additives can be used individually or in combination with other additives or any of the other components of staining compositions described herein.

In still further embodiments, any combination of the above components is included in staining compositions of the present invention.

Methods of Staining Specimens

Although staining agents are traditionally applied by oral administration, intravenous administration or direct injection into the area to be imaged, the present invention provides methods for staining intact tissue by incubation in the agent. The present inventors have found that although not traditionally thought to be able to penetrate intact tissue, certain staining agents are able to pass through tissue to stain the specimen such that the boundaries between bone and soft tissue can be differentiated using visualization methods such as microCT.

In an exemplary aspect, specimens are incubated for a selected period in a staining composition of the present invention. The period of time over which the specimen is incubated with the staining composition is readily determined by those of skill in the art and is informed by the level of contrast desired in the images acquired from the stained specimen. Incubation in staining compositions is generally conducted at ambient room temperature, but staining at higher and lower temperatures is also within the scope of the present invention.

In exemplary embodiments, the specimen is in contact with the staining compositions from about one hour to about one week. In still further exemplary embodiments, the specimen is in contact with the staining compositions for about nine hours to about five days, about twelve hours to about four days, about sixteen hours to about two days and about eighteen hours to about twenty-four hours. Periods of at least about three hours, at least about five hours, at least about ten hours and at least about fifteen hours are also of use in the methods of the invention In some embodiments, the specimen is serially stained with two or more staining compositions. In further embodiments, such serial staining is conducted using the same kinds of staining compositions or using different kinds of staining compositions. For example, in some embodiments, the preparation of a specimen for imaging comprises two separate PTA stains. In such embodiments, the specimen is stained for a period of time in a first staining composition comprising a PTA solution, and then re-stained in a second staining composition comprising a PTA solution. The first and second staining compositions may include identical PTA solutions or different PTA solutions. For example, the first staining compositions may include a 1% PTA solution whereas the second staining compositions may include a 1% PTA solution in combination with an additive such as calcium. As will be appreciated, serially staining as described herein can be conducted using staining compositions with any combinations of components described herein and known in the art.

In further embodiments, after incubation in a staining composition, specimens are transferred to one or a series of buffer solutions so as to remove extra staining agents and to create a density contrast between the specimens and the bordering environment to facilitate distinguishing of the tissue from its bordering environment. In some embodiments, the buffer has a different osmolality than that of the tissue to accelerate or otherwise enhance the transfer of stain molecules into components of the specimen, e.g., tissue cells. An exemplary buffer is a buffered saline solution, e.g., phosphate buffered saline (PBS). When this subsequent osmolality differential is applied, the staining composition can be of a greater or lesser osmolality than the buffer to which the stained specimen is subsequently submitted. Buffer solutions of use in the present invention can include without limitation sodium cacodylate buffer, phosphate-buffered saline, and ethanol solutions. In specific embodiments, transfers through buffers are conducted for the same or different periods of time. In further embodiments, these transfers (also referred to herein as "washes") through buffers are conducted for about one to about five hours.

In yet further embodiments, the stained specimen may further be submitted to treatment with an organic solvent or a mixture of an organic solvent in water. Exemplary organic solvents are those that are at least partially soluble in water and include, e.g., alcohols, ethers, esters and the like. The medium in which the specimen is suspended can be altered from a first mixture (e.g., the staining composition) to a final mixture (e.g., 100% organic solvent) in a single step or, alternatively, the change in specimen environment can be accomplished by submitting the stained specimen to a gradient of medium compositions, moving step-wise or continuously from the first mixture to the final mixture.

In some embodiments, specimens are fixed prior to contact with staining compositions. In some embodiments, specimens are fixed through incubation in a formalin solution for a period of time. In some embodiments, the formalin is a 10% neutral buffered formalin solution. In further embodiments, the formalin can range from a 0.5 to a 15% neutral buffered solution. In some embodiments, the specimen is fixed for a period of about two to four days. In further embodiments, the specimen is fixed for a period of about one day to about two weeks. In still further embodiments, the specimen may be fixed for a month or longer.

In further embodiments, specimens are washed prior to, subsequent to, or both prior to and subsequent to incubation in a staining composition. In still further embodiments, specimens are washed prior to, subsequent to, or both prior to and subsequent to pre-stain fixation in solutions such as formalin. In specific embodiments, these washes are conducted in phosphate buffered saline (PBS) for about one to about five hours. In still further embodiments, multiple washes are conducted.

The methods of the invention preferably provide stained specimens in which the density of the staining is essentially invariant from one border of the specimen to an antipodal border of the specimen. As used herein, the term "essentially invariant" refers to the homogeneity of the staining of a specimen. In a preferred embodiment, a specimen exhibiting essentially invariant staining will have a density of stain that varies by no more than about 20%, more preferably by no more than about 10% and still more preferably by more than about 5% across a line through the specimen from a point on one border of the specimen to the antipodal point on the opposite border of the specimen.

As will be appreciated, any combination of methods and staining compositions described herein can be used to prepare specimens for imaging. Although specific embodiments of staining compositions and methods are described herein, it is within the skill of one in the art to alter components and procedures described herein and known in the art in to prepare specimens for imaging modalities such a microCT virtual histology.

In a specific aspect, the present invention provides stains that are particularly suited for detection of atherosclerotic plaques. Atherosclerosis is a disease affecting arterial blood vessels caused by the formation of multiple plaques within the arteries. These plaques are generally formed from cells (mostly macrophage cells), or cell debris, which contain cholesterol, fatty acids, calcium and fibrous connective tissue. Plaque formation leads to a reduction of the arterial cross-section and to a diminution of the elasticity and contractility of the elastic muscular fibers in the zone where the plaque is formed.

In general, specimens for imaging of atherosclerotic plaques are stained in an electron dense staining agent. In specific embodiments, this electron dense staining agent is phosphotungstic acid (PTA). Although much of the following description focuses on the use of PTA for clarity's sake, it will be appreciated that the methods described herein apply to any other electron dense staining agent known in the art.

In further embodiments, a 5% PTA solution is used to stain specimens for detection of atherosclerotic plaques. In still further embodiments, a 1% to 20% PTA solution is used. In yet further embodiments, a: 2%-18%, 3%-16%, 4%-14%, 5%-12%, 6%-10%, and 7%-8% PTA solution is used. In some embodiments, the specimen is stained in a PTA solution for two days. In further embodiments, the specimen is stained from about twelve hours to about one week.

In yet further embodiments, the PTA solution is changed at least once during the staining process, for example, in embodiments where a specimen is stained in a PTA solution for two days, the PTA solution is replaced with fresh PTA solution each day.

In still further embodiments, the specimen is protected from light during the staining period.

In some embodiments, specimens are fixed prior to staining. Fixing specimens is known in the art and described in further detail above. For imaging of atherosclerotic plaques, specimens are in some exemplary embodiments fixed through incubation in a formalin solution for a period of time. In some embodiments, the formalin is a 10% neutral buffered formalin solution. In further embodiments, the formalin can range from a 0.5 to a 15% neutral buffered solution. In some embodiments, the specimen is fixed for a period of about two to four days. In further embodiments, the specimen is fixed for a period of about one day to about two weeks. In still further embodiments, the specimen may be fixed for a month or longer.

In further embodiments, specimens are washed prior to, subsequent to, or both prior to and subsequent to staining. In specific embodiments, these washes are conducted in phosphate buffered saline (PBS) for about one to about five hours. In still further embodiments, multiple washes are conducted prior to, subsequent to, or both prior to and subsequent to staining.

It will be appreciated that any of the above compositions and methods can be used in a variety of different combinations to provide an optimal image for a particular specimen. In some embodiments, a titration of the different components of the stains, washes and fixatives, as well as a titration of the lengths of time taken for each step of preparing the specimen, is conducted to identify the combination that produces an image with the best resolution.

In some embodiments, the specimen stained in accordance with any of the above methods is an intact dissection of an aorta, heart and at least a portion of a spine. Such intact dissections provide the advantage of maintaining the aorta in an open conformation, allowing for better resolution of any plaques within the aorta. Such intact dissections may be obtained, for example, from mammals such as mice and rats. In further embodiments, such dissections are obtained from embryonic mice or rats. In still further embodiments, such dissections are obtained from embryonic mice or rats at developmental stage E16 to P0.

In still further embodiments, prior to staining, incisions are made in the specimen to enhance penetration of the stain.

In yet further embodiments, the specimens are blanched prior to staining in order to remove extraneous tissue or membrane that may cause artifacts during image acquisition. In still further embodiments, incisions may be made in the specimen to enhance penetration of the stain after the specimen has been blanched.

Methods of Dissection and Further Preparation of Specimens for Staining

In an exemplary aspect of the invention, the specimen stained is a "solid tissue". As used herein, "solid tissue" refers to those tissues in which the parenchyma is present in an amount of at least about 50%. Solid tissue is distinct from tissue such as lung tissue. Specimens of the invention can include tissues, organs, as well as whole organisms (e.g., an embryo or a fetus).

In some embodiments, specimens stained according to the methods described herein are obtained from mammals such as rats and mice using dissection methods known in the art and described herein. In still further embodiments, specimens are prepared to enhance the penetration of the stains using blanching methods, incisions, and combinations of blanching and incisions.

In a further embodiment, penetration of staining compositions into a specimen is enhanced prior to or during treatment of the specimen with the staining composition. In an exemplary method, the porosity of the specimen is enhanced by chemical or physical methods. Exemplary chemical methods include osmotic disruption of the integrity of the specimen structure and treatment of the tissue with a penetration enhancing substance, e.g., DMSO. Physical means include, but are not limited to puncturing the specimen to form channels in the specimen through which the stain flows with greater facility than through corresponding undisrupted regions of the specimen. Channels can be formed in the specimen by puncturing it with an object or by subjecting it to focused energy, such as the light from a laser. in a general example of a staining process of the invention, a specimen, e.g., a cell, a tissue, an embryo, or a fetus, is stained to saturation for a selected period in a solution of 0.1 M buffer (pH 7.2), 1% fixative or cross-linking agent, and 1% staining agent, rocking at room temperature. The stained specimen is then washed and dehydrated. For example, specimens are washed for 30 minutes in 0.1M buffer, and twice more for 30 minutes in a second buffer providing an environment with an osmolality different from the staining solution and/or the washing buffer subsequent to the staining solution. Specimens are then incubated in a graded series of organic solvent concentrations to 100% organic solvent prior to imaging. An organic solvent is an example of a medium that increases the apparent density differences between the suspension medium and the stained tissue. In an exemplary staining process of the invention, a specimen, e.g., a cell, a tissue, an embryo, or a fetus, is stained to saturation overnight in a solution of 0.1 M sodium cacodylate (pH 7.2), 1% glutaraldehyde, and 1% osmium tetroxide, rocking at room temperature. The stained specimen is then washed and dehydrated. For example, specimens are washed for 30 minutes in 0.1 M sodium cacodylate buffer, and twice more for 30 minutes in phosphate-buffered saline. Specimens are then incubated in a graded series of ethanol concentrations to 100% ethanol prior to scanning. Ethanol is an example of a medium that increases the apparent density differences between the suspension medium and the stained tissue, thus further increasing the level of contrast in images obtained from specimens treated with such compositions.

Imaging Methods

In one aspect of the invention, images of specimens prepared according to methods described herein are obtained using, for example, bioluminescence imaging, planar gamma camera imaging, SPECT imaging, light-based imaging, magnetic resonance imaging and spectroscopy, fluorescence imaging (especially in the near infrared), diffuse optical tomography, ultrasonography (including untargeted microbubble contrast, and targeted microbubble contrast), PET imaging, fluorescence correlation spectroscopy, in vivo two-photon microscopy, optical coherence tomography, speckle microscopy, and microCT imaging. Massoud et al. provide a detailed review of molecular imaging technologies (Genes and Development, 17:545-580, 2003), which is herein incorporated in its entirety for its teaching regarding molecular imaging.

In a further aspect, microCT methods of the present invention provide high resolution, non-destructive analysis of the status, integrity and development of biological tissues. In specific aspects, virtual histology methods are conducted according to methods and compositions described in U.S. application Ser. No. 12/162,376, filed Oct. 15, 2008; Ser. No. 11/575,057, filed Jan. 29, 2008; Ser. No. 11/888,995, filed Aug. 3, 2007; Ser. No. 11/839,414, filed Aug. 15, 2007; Ser. No. 12/389,094, filed Feb. 19, 2009; 61/143,380, filed Jan. 8, 2009; and 61/230,574, filed Jul. 31, 2009, each of which is hereby incorporated by reference in its entirety, including all drawings, examples, and disclosure related to microCT virtual histology imaging and processing of virtual histology images.

The sensitivity and specificity of microCT-based analyses provides a rapid and inexpensive method that enhances visualization and analysis of complex global 3-dimensional organization. Unlike traditional histology, which requires meticulous slicing and individual examination, the methods of the present invention includes staining specimens with specific staining compositions as described herein and scanning them with microscopic computed tomography (microCT), which provides a high resolution image of the whole specimen without the need for the slices required in other imaging modalities. The methods of the present invention provide a digital visualization with the capability of providing a number of measurements of various anatomical features of the specimen. Such measurements include without limitation distance, area and volume of such anatomical features.

Although the following section provides a description of embodiments in terms of microCT imaging, it will be appreciated that these methods can be adapted to other imaging technologies using methods known in the art.

In specific embodiments, specimens prepared according to methods known in the art and described herein are scanned in an X-ray computed tomography scanner to provide microCT images of the specimens. Virtual histology imaging methods are described in International Publication No. WO/2007/089641, filed on Jan. 26, 2007 and U.S. application Ser. No. 11/575,057, filed Oct. 23, 2008, each of which is hereby incorporated by reference in its entirety for all purposes and in particular for all teachings related to microCT virtual histology.

A microCT image is generated, for example, using a commercially available scanner, such as an eXplore Locus SP microCT specimen scanner (GE Healthcare, London, Ontario) or the eXplore Locus RS small animal microCT scanner (GE Healthcare, London, Ontario). More rapid volumetric CT scans of specimens may be performed at lower resolution, such as at 27 micron$^3$ isometric voxel resolution, while longer higher resolution scans, such as 8 micron$^3$ isometric voxel resolution, may also be performed, depending on the desired cost, time constraints and resolution required.

Parameters such as current, voltage, and exposure time are adjusted as appropriate and are kept constant for images to be compared. For each scan, a number of evenly spaced views may be averaged. The scans may be filtered, for instance to avoid saturation of the detector, using appropriate filters, such as 0.2 mm aluminum.

Images can be reconstructed using appropriate software, such as EVSBeam© software. Preliminary visualizations and virtual histology sections may be generated with the publicly available Micro View© program. Isosurfaces renderings and volume renderings of the CT datasets can also be generated as images.

In an exemplary embodiment, specimen scans with resolution of 3 microns or better are obtained in less than 12 hours. For example, isometric resolutions of 27 microns or 8 microns are achieved with scan times of 2 hours or 12 hours. MicroCT-based virtual histology matches or exceeds the tissue contrast achieved by more time- and cost intensive magnetic resonance microscopy, while delivering more than 2-fold higher resolution' up to 8 microns for microCT, (Jacobs, R. E., et al., Comput Med Imaging Graph 23, 15-24 (1999), or in some cases up to 6 microns. For increased throughput of these types of studies, multiple specimens are optionally scanned simultaneously in the same field of view. For example, at lower microCT resolutions (27 microns), multiple specimens can be simultaneously scanned in approximately two hours with adequate quality for post-imaging segmentation analysis allowing the recognition of gross and subtle mutant phenotypes. For increased detail of abnormalities suspected on the low-cost 27 micron scans, the same stained specimens can later be scanned at 8 micron resolution for obtaining fine details such as organ sub-compartments and fine tissue structures.

The computed tomography image of a specimen, such as an organ or whole animal, may include an isosurface rendering so as to examine the exterior of the specimen for anatomical or molecular differences compared to other "control" specimens. In a further embodiment, the computed tomography image of the specimen may include a virtual section of the specimen.

Large numbers of images and associated data may be generated using micro computed tomography to image specimens. Such virtual histology datasets represent a valuable resource for investigating effects of certain experimental procedures, such as for example, genetic manipulation such as gene disruption or overexpression in vivo. However, generated datasets relating to one mutation or other variable at a particular stage of development or treatment may have further value when compared to a second mutation/variable or at a second stage. In order to facilitate access and aid in generation of such comparative data, a computer-based process for collecting, storing and retrieving micro computed tomography images and/or image data is provided according to the present invention. In one embodiment, such a process includes the steps of generating a digital computed tomography image, electronically transmitting the image and/or data to a centralized data storage location associated with a computer, retrieving the image and/or data from the storage location in response to a request and electronically displaying or transmitting the image and/or data and/or analysis of the image and/or data to a second location in response to the request.

A generated computed tomography image and/or data for generating such an image may be stored electronically, in memory circuitry such as a database, and/or on a computer readable storage medium. A generated computed tomography image is communicated to a repository for such images, a centralized image and/or image data storage location associated with a computer. Thus, for example, three-dimensional reconstructions of transgenic and wild-type mouse embryos are generated and images and/or data for image generation is sent to a centralized storage location associated with a computer. Such images and data for image generation may be generated and communicated from multiple locations for centralized storage.

Communication of generated images and/or image data is may be conducted over a wired or wireless connection to a device or system configured as a server or computer network accessible by multiple users from multiple locations. The server or computer network may include any type of computer device or devices such as a personal computer, workstation or mainframe computer.

Processing and memory circuitry is included in the server or computer network such that an image and/or image data may be communicated to memory circuitry and stored. Further, the stored information may be retrieved from the memory circuitry. Optionally included is a comparison program executable by the circuitry to carry out a comparison of one images or set of images with another set of images in order to characterize differences between the images relating to anatomical and/or molecular differences in specimens imaged. Such a comparison program may be stored and executed on a server or computer network which also includes the stored image and/or image data. A comparison program may also be stored and executed by a separate device to which images and/or image data retrieved from the memory circuitry of the server or computer network are downloaded.

An image and/or data for generating an image may be retrieved from the centralized storage location in response to a request. For example, a user inputs information to a device having data input and output capacity to communicate a request to retrieve an image and/or image data from the server or computer network storage location. The image and/or data may be displayed to the user and/or downloaded to the user's device. Further, the retrieved image and/or data may be retrieved for analysis and results of the analysis displayed or downloaded to the user.

In some embodiments, multiple images of different specimens or multiple images taken at different times of the same specimen will be compared to identify differences and similarities in anatomical features. In such embodiments, methods can be used to ensure that the images are co-registered to identify points in each image which correspond to points in the other images. Registration of images is a fundamental task in image processing used to match two or more pictures taken, for example, at different times, from different sensors, or from different viewpoints. Registration techniques are known in the art. (see, e.g., Brown., (1992), ACM Computing Surveys, 24(4): 325-76), and are also described in U.S. application Ser. No. 11/839,414, filed on Aug. 15, 2007, which is hereby incorporated by reference in its entirety for all purposes and in particular for all teachings related to image processing and comparing multiple images to each other and to reference images.

EXAMPLES

Example 1

Aortic Arch Stain for Atherosclerotic Plaque (Mouse)

The specimen for the aortic arch stain was provided by dissecting a mouse using standard methods to provide the aorta, heart and a portion of the spine as an intact sample.

The specimen was washed in PBS three times. Each wash was an hour long, and the PBS solution was exchanged for fresh solution after each wash.

The specimen was then fixed in a 10% neutral buffered formalin solution for three days.

The specimen was removed from the formalin solution and placed in a 5% PTA stain for two days. The PTA solution was exchanged for fresh solution every day of the staining period.

The specimen was then again washed in PBS three times—each wash was an hour long and the solution was exchanged for fresh PBS solution after each wash.

After the final wash, the specimen was imaged using a microCT scan. FIG. 1 shows an image of an aorta with no atherosclerotic plaques present (left panel) and an image of an aorta with atherosclerotic plaques present, indicated by the arrow (right panel).

Example 2

Preparing Specimens for Staining

In order to increase penetration of one or more stains in a specimen, the specimen may be blanched and/or incisions can be made in the specimens prior to staining.

When using whole animal specimens, for example E16 to P0 mice or rats, the specimen can be blanched and/or incisions may be made to open the thoracic pleura, abdominal peritoneum, and/or dura mater to further enhance stain penetration after skin removal.

The procedure for blanching the specimen can include making a small shallow "x" cut on the ventral and dorsal sides of the specimen. The specimen is placed in boiling water for approximately 10 to 12 seconds and then doused in ice water. A cotton tip swab or other implement can be used to gently rub the epidermis/dermis off of the specimen. Alternatively, the skin may be peeled from the specimen using fine forceps under a dissecting microscope. In order to remove extraneous membrane and tissue, the specimen may be further sealed in a container containing a solution such as PBS and placed on a rocking shaker for two to ten minutes. The treatment with PBS and the rocking shaker may be repeated multiple times as needed.

In addition to blanching, incisions may be made in the specimen to further enhance the penetration of the stain into tissues of interest.

To open the thoracic pleura, a short supracostal incision can be made with a scalpel above the 10th rib on the left lateral side of the body. Since nerves and vessels run below each rib, making the incision above the rib will less likely cause damage to a vessel and avoid unwanted hemorrhages. Additionally, since the 10th rib is located anterior-lateral to the gap between the lungs and the diaphragm, making the incision above the 10th rib will be less likely to cause damage to internal structures.

Using scissors with the tips up, the cut is extended along the top edge of the 10th rib to approximately 2-4 mm in length without damaging internal structures such as the lungs and heart.

The supracostal incision/cut is then repeated for the right lateral side of the body. The cut is generally no deeper than 1 mm from the surface in order to open only the thoracic pleura and not damage any internal organs.

To open the peritoneum, a small vertical incision can be made with a scalpel along the midline of the abdominal cavity approximately 1 mm above the umbilicus. Using micro-scissors with the tips up, the incision is extended to approximately 1.3 mm in length in the direction of the xiphoid process, cutting only the abdominal peritoneum without damaging any internal organs. The incision is generally less than 1.3 mm in length to ensure that the cut is inferior to the liver, thereby making it less likely that the liver is damaged. The cut is also generally no deeper than 0.3 mm from the surface to prevent damage to the intestines.

To open the dura mater, a 2-3 mm long incision with a scalpel can be made along the suture of the skull. The cut is generally no deeper than 0.5 mm from the surface in order to open the dura mater without damaging other structures in the brain.

Once all incisions are completed, the specimen can be transferred to a staining or fixing solution for further processing.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are herein incorporated by reference in their entirety for all purposes.

I claim:

1. A method for detecting an atherosclerotic plaque, said method comprising:
    (a) incubating a specimen in a staining composition to produce a stained specimen, wherein said specimen comprises an aorta, heart and at least a portion of spine as an intact dissected sample, and wherein said staining composition comprises a 5% phosphotungstic acid (PTA) solution; and
    (b) scanning said stained specimen in an X-ray tomography scanner to produce a microCT image of said stained specimen,
    thereby detecting said atherosclerotic plaque.

2. The method of claim 1, wherein prior to said incubating step (a), said specimen is fixed in a 10% neutral buffered formalin solution.

3. The method of claim 1, wherein prior to said incubating step (a), said specimen is washed in a phosphate buffered saline (PBS) solution.

4. The method of claim 1, wherein said incubating is conducted for at least two days.

* * * * *